(12) United States Patent
Lohstreter et al.

(10) Patent No.: US 12,094,661 B2
(45) Date of Patent: Sep. 17, 2024

(54) FEEDTHROUGH FERRULE WITH BEVELED LEDGE

(71) Applicant: Medtronic, Inc., Minneapolis, MN (US)

(72) Inventors: Lance B. Lohstreter, Brooklyn Park, MN (US); Jonathan R. Alvin, Lino Lakes, MN (US); Joel D. Hoepner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 327 days.

(21) Appl. No.: 17/583,878

(22) Filed: Jan. 25, 2022

(65) Prior Publication Data

US 2023/0238185 A1     Jul. 27, 2023

(51) Int. Cl.
*H01G 4/35*     (2006.01)
*A61N 1/375*     (2006.01)

(52) U.S. Cl.
CPC ............. *H01G 4/35* (2013.01); *A61N 1/3754* (2013.01)

(58) Field of Classification Search
CPC .......... H01G 4/35; H01G 4/38; A61N 1/3754; A61N 1/3758
USPC ....................................................... 174/650
See application file for complete search history.

(56) References Cited

U.S. PATENT DOCUMENTS

| | | |
|---|---|---|
| 6,765,780 B2 | 7/2004 | Brendel et al. |
| 7,930,032 B2 | 4/2011 | Teske et al. |
| 8,675,338 B2 | 3/2014 | Teske |
| 10,874,866 B2 | 12/2020 | Stevenson et al. |
| 2006/0085043 A1 | 4/2006 | Stevenson |
| 2006/0175071 A1 | 8/2006 | Knappen et al. |

FOREIGN PATENT DOCUMENTS

WO     2019/090298     5/2019

OTHER PUBLICATIONS

International Search Report and Written Opinion for PCT/IB2023/050030 dated Mar. 27, 2023 (10 pages).

*Primary Examiner* — Tremesha S Willis
(74) *Attorney, Agent, or Firm* — Mueting Raasch Group

(57) ABSTRACT

A feedthrough component includes a feedthrough ferrule including a ferrule body extending from a proximal end to a distal end along a longitudinal axis of the feedthrough ferrule and a ferrule passageway extending through the ferrule body and defined by a plurality of sidewalls. The ferrule passageway includes a proximal passage portion defined by one or more proximal sidewalls of the plurality of sidewalls and extending along the longitudinal axis, a distal passage portion defined by one or more distal sidewalls and extending along the longitudinal axis, and a beveled ledge disposed between the proximal passage portion and the distal passage portion and extending from the one or more distal sidewalls toward the longitudinal axis of the feedthrough ferrule. The beveled ledge includes a beveled surface extending toward the longitudinal axis, where a normal to the beveled surface intersects the longitudinal axis.

20 Claims, 8 Drawing Sheets

FEEDTHROUGH FERRULE WITH BEVELED LEDGE

TECHNICAL FIELD

This disclosure generally relates to electrical components for hermetically sealed devices and feedthrough assemblies of such devices.

BACKGROUND

Various systems require electrical coupling between electrical devices disposed within a sealed enclosure or housing and devices or systems external to the enclosure. Oftentimes, such electrical coupling needs to withstand various environmental factors such that a conductive pathway or pathways from the external surface of the enclosure to within the enclosure remains stable. For example, implantable medical devices (IMDs), e.g., cardiac pacemakers, defibrillators, neurostimulators, and drug pumps, which include electronic circuitry and one or more power sources, require an enclosure or housing to contain and seal these elements within a body of a patient. Many of these IMDs include one or more electrical components such as, for example, feedthrough assemblies to provide electrical connections between the elements contained within the housing and components of the IMD external to the housing, for example, one or more sensors, electrodes, and lead wires mounted on an exterior surface of the housing, or electrical contacts housed within a connector header, which is mounted on the housing to provide coupling for one or more implantable leads. One example of apparatus that can provide an electrical coupling between electrical devices disposed within a sealed enclosure or housing and devices or systems external to the enclosure is a feedthrough ferrule.

Feedthrough ferrules may include a ferrule body and a feedthrough pin extending through the ferrule body. To comply with electrical standards and/or provide appropriate functionality, a direct current (DC) resistance between the ferrule body and the feedthrough pin of at least 50 gigaohms may be required.

SUMMARY

The techniques of this disclosure generally relate to feedthrough ferrules for feedthrough assemblies. Ferrule bodies of such feedthrough ferrules include a beveled ledge that may prevent the formation of an electrical short or a low resistance DC electrical connection between the ferrule body and a feedthrough pin of the feedthrough ferrule during a welding or heating step of constructing the feedthrough ferrule or a feedthrough assembly that includes the feedthrough ferrule. The beveled ledge of the feedthrough ferrule may prevent the formation of an enclosed pocket between a capacitor of the feedthrough ferrule and an insulator formed between the feedthrough pin and the ferrule body. Enclosed pockets that may be formed in existing feedthrough ferrules may result in an area of relatively low pressure that can pull low resistance material (e.g., liquified or wetted solder) into contact with both the ferrule body and the feedthrough pin during welding or heating of the feedthrough ferrule and forming an electrical short between the ferrule body and the feedthrough pin. Accordingly, feedthrough ferrules that include a beveled ledge as described herein, may prevent the formation of an electrical short between the ferrule body and the feedthrough pin during device construction, thereby preventing or reducing failures of feedthrough assemblies that include such feedthrough ferrules.

In one example, aspects of this disclosure relate to a feedthrough component including a feedthrough ferrule, a feedthrough pin, and a capacitor. The feedthrough ferrule includes a ferrule body and a ferrule passageway. The ferrule body extends from a proximal end to a distal end along a longitudinal axis of the feedthrough ferrule. The ferrule passageway extends through the ferrule body and is defined by a plurality of sidewalls. The ferrule passageway includes a proximal passage portion, a distal passage portion, and a beveled ledge. The proximal passage portion is defined by one or more proximal sidewalls of the plurality of sidewalls and extends along the longitudinal axis. The distal passage portion is defined by one or more distal sidewalls and extends along the longitudinal axis. The beveled ledge is disposed between the proximal passage portion and the distal passage portion and extends from the one or more distal sidewalls toward the longitudinal axis of the feedthrough ferrule. The beveled ledge includes a beveled surface extending toward the longitudinal axis. A normal to the beveled surface intersects the longitudinal axis. The feedthrough pin extends through the ferrule passageway and is coupled to the one or more proximal sidewalls. The capacitor is disposed in the distal passage portion and is electrically coupled to the feedthrough pin and the one or more distal sidewalls.

In another example, aspects of this disclosure relate to a feedthrough assembly including a substrate and one or more feedthrough components extending through the substrate. Each of the one or more feedthrough components includes a feedthrough ferrule, a feedthrough pin, and a capacitor. The feedthrough ferrule includes a ferrule body and a ferrule passageway. The ferrule body extends from a proximal end to a distal end along a longitudinal axis of the feedthrough ferrule. The ferrule passageway extends through the ferrule body and is defined by a plurality of sidewalls. The ferrule passageway includes a proximal passage portion, a distal passage portion, and a beveled ledge. The proximal passage portion is defined by one or more proximal sidewalls of the plurality of sidewalls and extends along the longitudinal axis. The distal passage portion is defined by one or more distal sidewalls and extends along the longitudinal axis. The beveled ledge is disposed between the proximal passage portion and the distal passage portion and extends from the one or more distal sidewalls toward the longitudinal axis of the feedthrough ferrule. The beveled ledge includes a beveled surface extending toward the longitudinal axis. A normal to the beveled surface intersects the longitudinal axis. The feedthrough pin extends through the ferrule passageway and is coupled to the one or more proximal sidewalls. The capacitor is disposed in the distal passage portion and is electrically coupled to the feedthrough pin and the one or more distal sidewalls.

In another example, aspects of this disclosure relate to an implantable medical device including a feedthrough housing, a substrate hermetically sealed to the feedthrough housing, and one or more feedthrough components extending through the substrate. Each of the one or more feedthrough components includes a feedthrough ferrule, a feedthrough pin, and a capacitor. The feedthrough ferrule includes a ferrule body and a ferrule passageway. The ferrule body extends from a proximal end to a distal end along a longitudinal axis of the feedthrough ferrule. The ferrule passageway extends through the ferrule body and is defined by a plurality of sidewalls. The ferrule passageway includes a proximal passage portion, a distal passage portion, and a beveled ledge. The proximal passage portion is defined by one or more proximal sidewalls of the plurality of sidewalls and extends along the longitudinal axis. The distal passage portion is defined by one or more distal sidewalls and extends along the longitudinal axis. The beveled ledge is disposed between the proximal passage portion and the distal passage portion and extends from the one or more distal sidewalls toward the longitudinal axis of the feedthrough ferrule. The beveled ledge includes a beveled surface extending toward the longitudinal axis. A normal to the beveled surface intersects the longitudinal axis. The feedthrough pin extends through the ferrule passageway and is coupled to the one or more proximal sidewalls. The capacitor is disposed in the distal passage portion and is electrically coupled to the feedthrough pin and the one or more distal sidewalls.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.)

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1 is a schematic cross-sectional view of a feedthrough component without a beveled ledge prior to a welding or heating step.

FIG. 2 is a schematic cross-sectional view of the feedthrough component of FIG. 1 after a welding or heating step.

FIG. 3 is a schematic perspective view of a feedthrough component that includes a beveled ledge.

FIG. 4 is a schematic cross-sectional view of the feedthrough component of FIG. 3.

FIG. 5 is a schematic cross-sectional view of a feedthrough ferrule of the feedthrough component of FIGS. 3 and 4.

FIG. 6 is a schematic cross-sectional view of a feedthrough ferrule with a beveled ledge including a first surface and a beveled surface.

FIG. 7 is a schematic cross-sectional view of a feedthrough ferrule with a beveled ledge including a first surface, a beveled surface, and a second surface.

FIG. 8 is a schematic cross-sectional view of a feedthrough ferrule with a beveled ledge including a beveled surface that is convex.

FIG. 9 is a schematic cross-sectional view of a feedthrough ferrule with a beveled ledge including a beveled surface that is concave.

DETAILED DESCRIPTION

Figure 1:
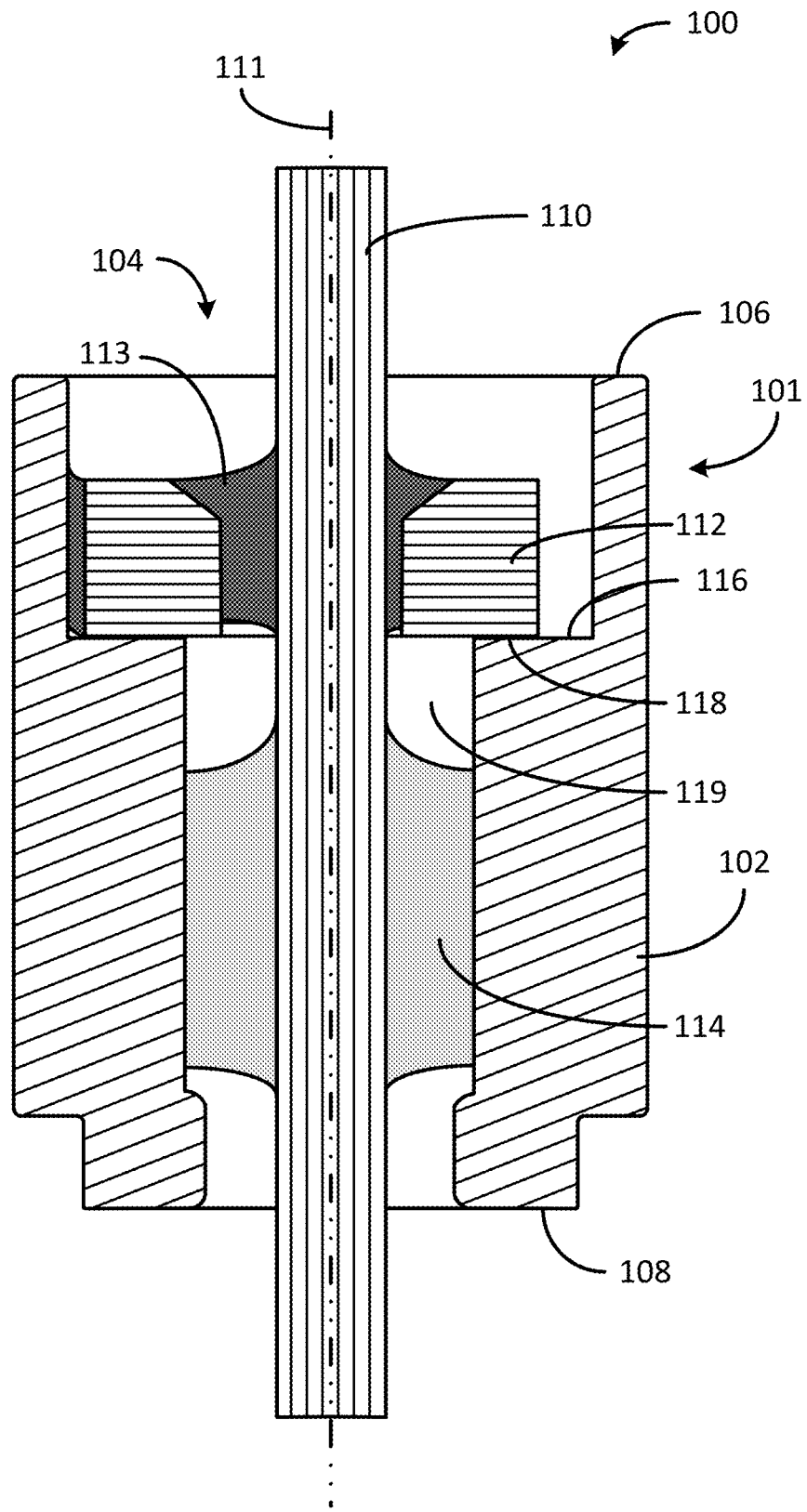
FIGS. 1 and 2 are schematic cross-sectional views of a feedthrough component that does not include a beveled ledge.

In general, the present disclosure provides various embodiments of feedthrough ferrules that include a beveled ledge and devices and systems that include such feedthrough ferrules. The feedthrough ferrules described herein may include a beveled ledge that prevents low pressure areas from developing that may pull conductive materials into contact with both a ferrule body and a feedthrough pin of the feedthrough ferrules. Accordingly, feedthrough ferrules with a beveled ledge may prevent the formation of electrical shorts between the ferrule body and the feedthrough pin of such feedthrough ferrules. As used herein, the term "electrical short" may refer to an electrical connection along an unintended path with a resistance less than that dictated by device specifications. In at least one embodiment, an electrical short may refer to a resistance of less than 50 gigaohms.

Feedthrough ferrules may include a ferrule body and a ferrule passageway that extends through the ferrule body. A feedthrough pin may extend through the ferrule passageway, and the feedthrough pin may be fixed relative to the ferrule body by an insulator or insulative material. Such insulative material may also provide or contribute to a hermetic seal between the ferrule body and the feedthrough pin. A capacitor may be disposed in the ferrule passageway, where a first terminal of the capacitor may be electrically and mechanically coupled to the ferrule body and a second terminal of the capacitor electrically and mechanically coupled to the feedthrough pin with a conductive material. The ferrule passageway may include a beveled ledge extending inward toward a longitudinal axis of the feedthrough ferrule such that at least a portion of the beveled ledge does not extend perpendicular to the longitudinal axis of the feedthrough ferrule. At least a portion of the beveled ledge may be arranged between the capacitor and the insulative material or seal.

The beveled ledge may prevent the formation of a low-pressure pocket between the capacitor and the insulative material or seal when the feedthrough ferrule is welded or heated. Various steps throughout the construction of a feedthrough assembly or an implantable medical device may heat the feedthrough ferrule, causing air within the ferrule passageway to expand. The beveled ledge may provide an air gap (e.g., an unobstructed passageway) that provides a path between a portion of the capacitor and sidewalls of the ferrule passageway. Accordingly, as the conductive material melts due to heat applied to the feedthrough ferrule, any pressure differentials that develop may cause airflow through the air gap rather than pulling conductive material into space between the capacitor and the insulative material. Thus, potential electrical shorts between the ferrule body and the feedthrough pin may be avoided. Accordingly, feedthrough ferrules with a beveled ledge may prevent or reduce failures of feedthrough assemblies or implantable devices caused by electrical shorts between the feedthrough pin and ferrule body of feedthrough ferrules.

Figure 2:
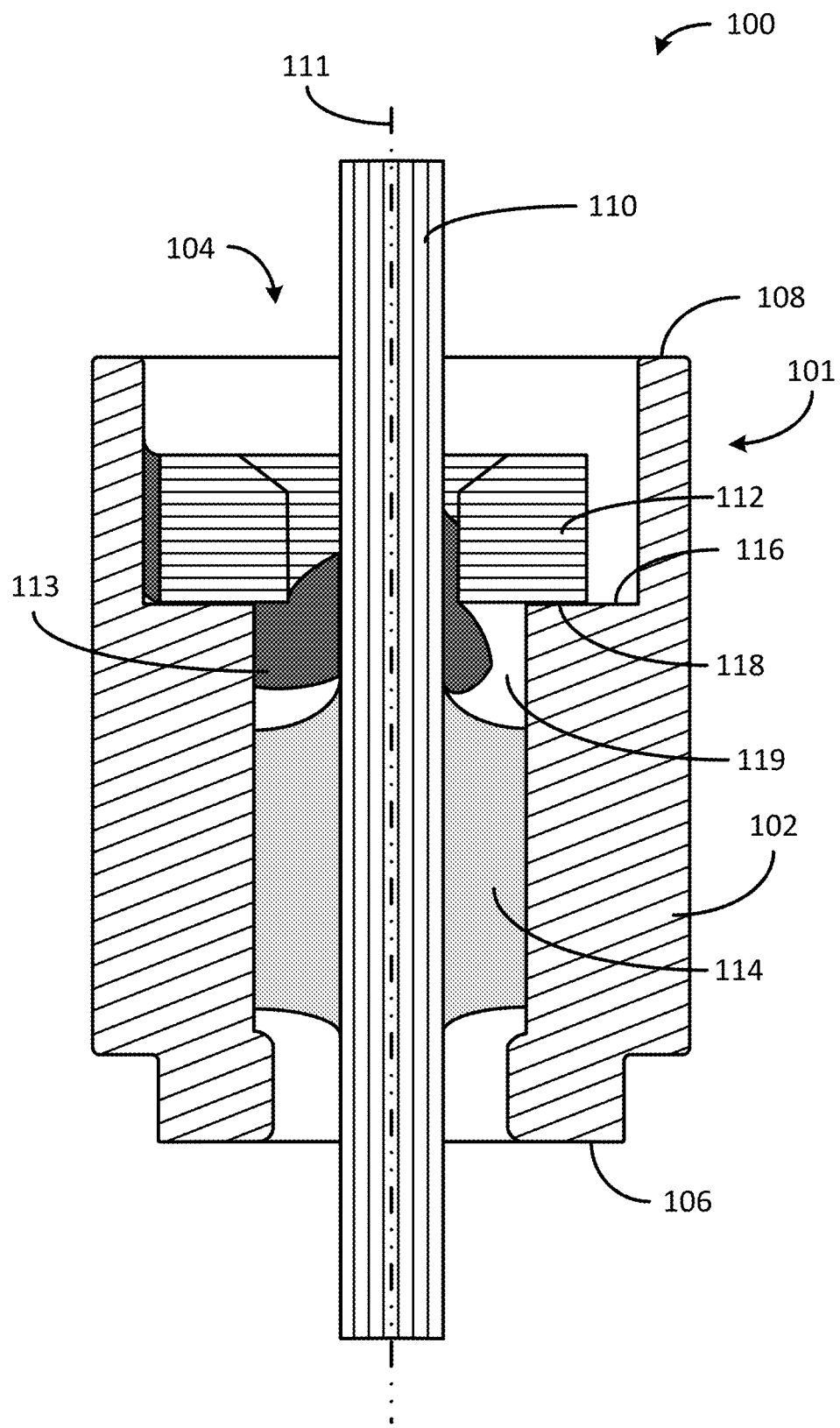

Existing feedthrough ferrules may form an electrical short between the ferrule body and the feedthrough pin when heated. One example of an existing feedthrough component 100 that does not include a beveled ledge is shown in FIGS. 1 and 2. FIG. 1 shows a schematic cross-sectional view of the feedthrough component 100 prior to a welding or heating step in a method or process for constructing a feedthrough assembly or implantable medical device. FIG. 2 shows a schematic cross-sectional view of the feedthrough component 100 of FIG. 1 after such a welding or heating step. In contrast with feedthrough ferrules that include a beveled ledge as described herein, feedthrough component 100 may be susceptible to failure via electrical shorting.

The feedthrough component 100 includes a feedthrough ferrule 101, a feedthrough pin 110, and a capacitor 112. The feedthrough ferrule 101 includes a ferrule body 102 and ferrule passageway 104. The ferrule body extends along a longitudinal axis 111 from a proximal end 108 to a distal end 106. The ferrule passageway 104 extends through the ferrule body 102. The feedthrough pin 110 extends through the ferrule passageway 104 and is coupled to the ferrule body 102 by insulative material 114. The insulative material 114 may provide a hermetic seal between the ferrule body 102 and the feedthrough pin 110.

The feedthrough component 100 also includes a capacitor 112 disposed within the ferrule passageway 104 and coupled to the ferrule body 102 and the feedthrough pin 110 via conductive material 113 (e.g., solder). The conductive material 113 may electrically and mechanically couple the capacitor 112 to the ferrule body 102 and the feedthrough pin 110. The ferrule passageway 104 includes a flat ledge 116. The flat ledge 116 may seat or position the capacitor 112 spaced apart from the insulative material 114. The capacitor 112 may form a 360 degree contact with the flat ledge 116. In other words, there may be no air gap between the capacitor 112 and the flat ledge 116. Additionally, the flat ledge 116 may form a seal 118 with flat portions of the capacitor 112. The seal 118 may not be a hermetic seal and may only be as strong as the contact pressure between the capacitor 112 and the flat ledge 116. The seal 118, the conductive material 113, and the insulative material 114 may form a pocket 119. Such an arrangement may provide a feedthrough component 100 that is susceptible to electrical shorting when heat is supplied to the feedthrough component 100.

When heat is supplied, for example, as a heat pulse to the proximal end 108 of the ferrule body, the pocket 119 may heat up and air in the pocket 119 may expand while the conductive material 113 is still solid. As such air expands, some of the air may escape the pocket 119 via seal 118 as the air pressure of the pocket 119 exceeds the contact pressure between the capacitor 112 and the flat ledge 116. As heat travels through the feedthrough component 100, the pocket 119 may begin to cool at about the same time the conductive material 113 melts or liquefies. As the pocket 119 cools a negative pressure may develop in the pocket 119. Accordingly, the now liquified conductive material 113 may be pulled into the pocket 119 due to such negative pressure. In other words, prior to the conductive material 113 becoming liquid, the seal 118 may be the path of least resistance for fluid movement along a pressure gradient between the pocket 119 and an external environment of the feedthrough component 100. However, once the conductive material 113 is liquified, the path of least resistance for fluid movement across such pressure gradient becomes the space occupied by the liquid conductive material 113. Thus, the pressure gradient induced by the application of heat to the feedthrough component 100 may pull conductive material into the pocket 119 that can cause an electrical short between the ferrule body 102 and the feedthrough pin 110. In contrast, feedthrough ferrules that include a beveled ledge as described herein may prevent or reduce such electrical shorts between ferrule bodies and feedthrough pins.

Figure 3:
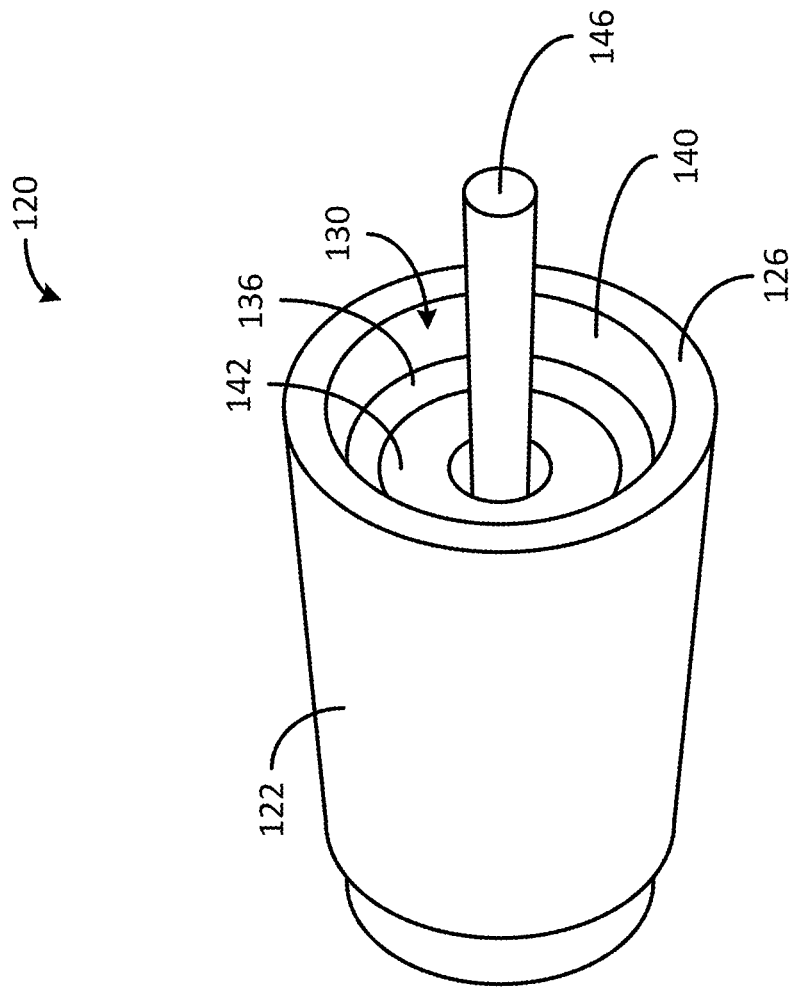
FIGS. 3-5 show a feedthrough component that includes a beveled ledge.
Figure 4:
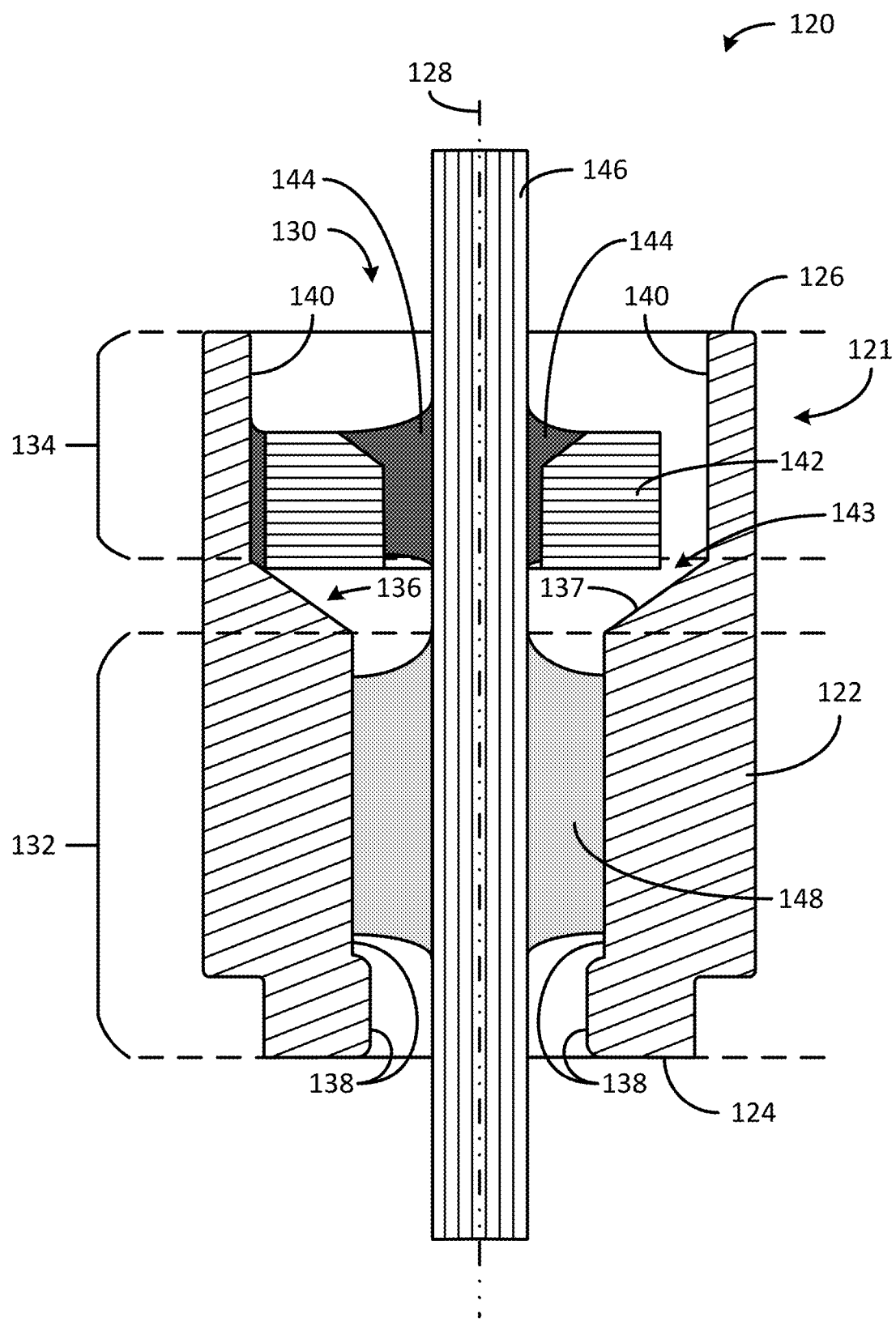
Figure 5:
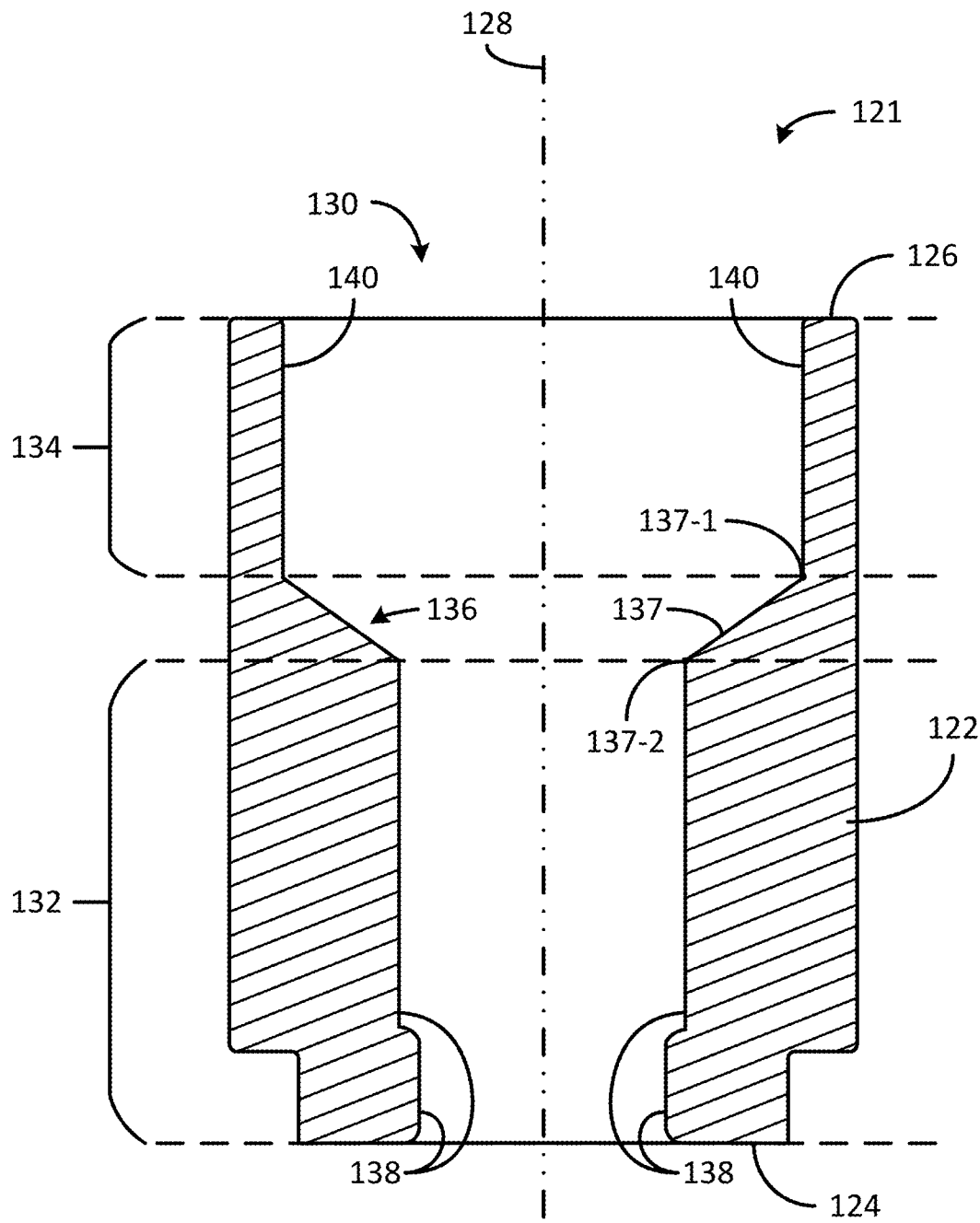

Feedthrough ferrules that include beveled ledges are shown in FIGS. 3-9. FIG. 3 shows a schematic perspective view of a feedthrough component 120 that includes a beveled ledge 136. FIG. 4 shows a schematic cross-sectional view of a feedthrough component 120 of FIG. 3. FIG. 5 shows a schematic cross-sectional view of a feedthrough ferrule 121 of the feedthrough component 120 of FIGS. 3 and 4 with additional components of the feedthrough component 120 removed. Additionally, FIGS. 6-9 show feedthrough ferrules with various embodiments of the beveled ledge 136.

The feedthrough component 120 includes a feedthrough ferrule 121, a feedthrough pin 146, and a capacitor 142. The feedthrough ferrule 121 includes a ferrule body 122 and a ferrule passageway 130. As shown, the feedthrough ferrule 121 is generally cylindrical. In other words, a cross-section of the feedthrough ferrule 121 perpendicular to a longitudinal axis 128 of the feedthrough ferrule 121 has a constant outer diameter (e.g., a circular cross section). However, the feedthrough ferrule 121 may take on any suitable size or shape. Generally, the shape of the feedthrough ferrule 121 is defined by the ferrule body 122.

The ferrule body 122 extends from a proximal end 124 to a distal end 126 along the longitudinal axis 128 of the feedthrough component 120. The ferrule body 122 may take on any suitable size or shape. The ferrule body 122 may be, for example, cylindrical, frustoconical, prismatic, cuboid, or any combination thereof. For example, some portions of the ferrule body 122 may be cylindrical while other portions may be frustoconical (e.g., a portion that tapers from one outer diameter to another). In at least one embodiment, the ferrule body 122 is cylindrical. As shown, the ferrule body 122 is cylindrical with a first outer diameter and a second outer diameter smaller than the first outer diameter. The first outer diameter extends from the distal end 126 along a majority of the length of the ferrule body 122. In contrast, the second outer diameter extends from the proximal end 124 only a short distance. As shown, the outer diameter of the ferrule body 122 does not taper between the first outer diameter and the second outer diameter. Instead, from the outside, the ferrule body 122 has the appearance of two cylinders that abut end to end forming a notch at and near the proximal end 124.

The ferrule body 122 may include any suitable material or materials. The ferrule body may include, for example, titanium, aluminum, vanadium, etc. In at least one embodiment, the ferrule body 122 includes titanium. Materials of the ferrule body 122 may be chosen to facilitate a hermetic seal between insulative or electrically nonconductive materials. Additional considerations may include the ability of such materials to maintain a shape of the ferrule body 122 while undergoing stress in the form of heat and pressure while also have a hollow interior or passageway therethrough (e.g., the ferrule passageway 130).

The ferrule passageway 130 extends through the ferrule body 122 and is defined by a plurality of sidewalls 138, 140. The plurality of sidewalls 138, 140 may be inner surfaces of the ferrule body 122. The ferrule passageway 130 includes a proximal passage portion 132, a distal passage portion 134, and a beveled ledge 136. The proximal passage portion 132 is defined by one or more proximal sidewalls 138 of the plurality of sidewalls and extends along the longitudinal axis 128. The distal passage portion 134 is defined by one or more distal sidewalls 140 and extends along the longitudinal axis 128.

Each of the proximal passage portion 132 and the distal passage portion 134 may include one or more diameters or cross-sectional areas that are arranged perpendicular to the longitudinal axis 128. The one or more diameters or cross-sectional areas of the proximal passage portion 132 may be defined by the one or more proximal sidewalls 138. Similarly, the one or more diameters or cross-sectional areas of the distal passage portion 134 may be defined by the one or more distal sidewalls 140. As shown, diameters or cross-sectional areas of the proximal passage portion 132 are smaller than a diameter or cross-sectional area of the distal passage portion 134. However, the diameters or cross-sectional areas of the proximal passage portion 132 and the distal passage portion 134 may be equal to one another. Furthermore, the diameter or cross-sectional area of the proximal passage portion 132 may be greater than the diameter or cross-sectional area of the distal passage portion 134. Still further, the diameters or cross-cross section areas of the proximal passage portion 132 and the distal passage portion 134 may vary along the length of such portions. For example, such diameters or cross-cross sectional areas may be tapered when the plurality of sidewalls 138, 140 extend non-parallel to the longitudinal axis 128. Further, for example, when the plurality of sidewalls 138, 140 are stepped similar to the one or more proximal sidewalls 138 as shown in FIGS. 4 and 5.

The beveled ledge 136 is disposed between the proximal passage portion 132 and the distal passage portion 134. Additionally, the beveled ledge 136 extends from the one or more distal sidewalls 140 toward the longitudinal axis 128. Furthermore, the beveled ledge 136 includes a beveled surface 137 extending toward the longitudinal axis 128. The beveled surface 137 may extend towards the longitudinal axis 128 at a non-perpendicular angle relative to the longitudinal axis or be curved in some manner. Additionally, a normal to the beveled surface 137 intersects the longitudinal axis 128. The normal to the beveled surface may define an acute angle relative to the longitudinal axis of at least 10 degrees and no greater than 70 degrees. As shown in FIGS. 4 and 5, the beveled surface 137 is planar. The beveled surface 137 may extend from a first endpoint 137-1 of the beveled surface 137 and a second endpoint 137-2 of the beveled surface 137 (see FIG. 5). As shown in FIGS. 4 and 5, the beveled ledge 136 defines a tapering frustoconical sidewall.

Figure 6:
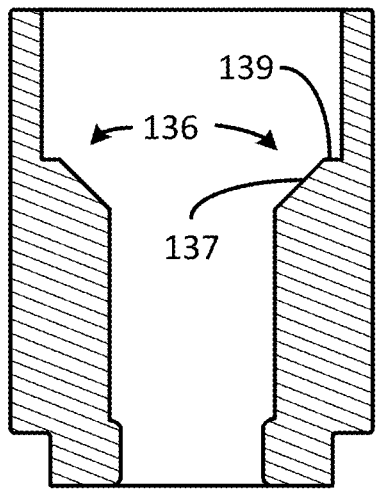
FIGS. 6-9 are schematic cross-sectional views of various embodiments of a feedthrough ferrule that include a beveled ledge.
Figure 7:
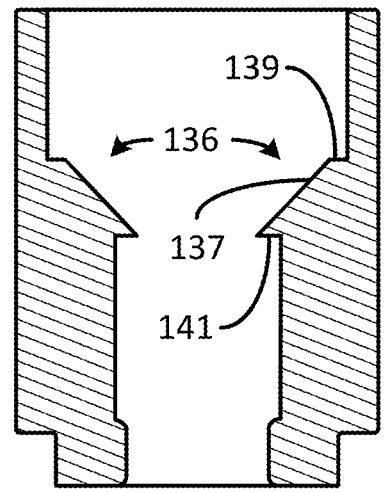

The beveled ledge 136 can take on any suitable size or shape. Although FIGS. 4 and 5 show the beveled ledge 136 with a single planar surface (beveled surface 137), the beveled ledge 136 may include any number of suitable planar or curved surfaces. For example, as shown in FIG. 6, the beveled ledge 136 can include a first surface 139, and the beveled surface 137. As shown in FIG. 6, the first surface 139 extends from the one or more distal sidewalls 140 and the beveled surface 137 extends from the first surface 139. Furthermore, the first surface 139 and the beveled surface 137 are non-coplanar. Instead, the first surface 139 extends perpendicularly towards the longitudinal axis 128 and the beveled surface 137 extends towards the longitudinal axis through a plane that forms an acute angle with the longitudinal axis 128 of at least 20 degrees and no greater than 80 degrees. Further, for example, the beveled ledge 136 may also include a second surface 141 as shown in FIG. 7. The second surface 141 may extend between the one or more proximal sidewalls 138 to the beveled surface 137 as shown in FIG. 7.

Figure 8:
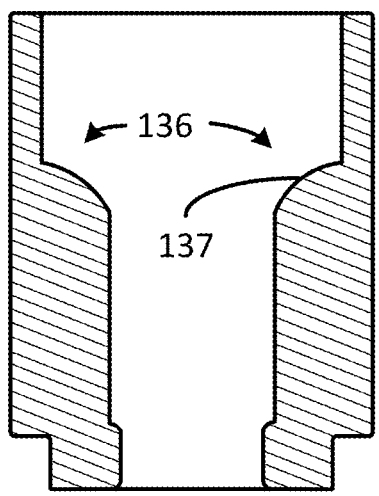
Figure 9:
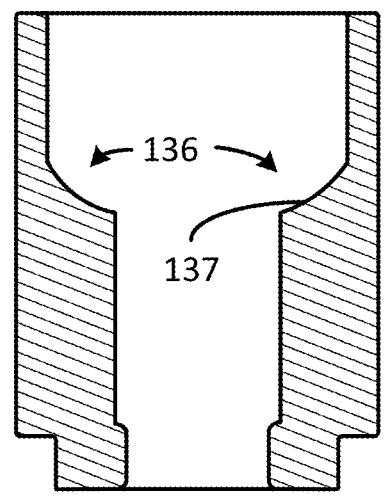

Although the beveled surface 137 is depicted as planar in FIGS. 4-7, the beveled surface 137 can also be curved. For example, the beveled surface can be convex as shown in FIG. 8 or concave as shown in FIG. 9. Additionally, the beveled surface 137 may include one or more surface features (not shown). Surface features may include, for example, a serpentine portion (e.g., convex and concave portions), ridges, bumps, dimples, or other surface shapes or features. Regardless of any surface feature or curvature the beveled surface 137, a plane that intersects both the first endpoint 137-1 of the beveled surface 137 and a second endpoint 137-2 of the beveled surface 137 may form an acute angle with the longitudinal axis of at least 20 degrees and no greater than 80 degrees. In at least one embodiment, the beveled surface 137 is planar. In at least one embodiment, the beveled surface 137 is convex.

As shown in FIGS. 3-5, the beveled ledge 136 is continuous. In other words, when viewed along the longitudinal axis 128, the beveled ledge 136 may appear to define an unbroken circumference or perimeter. However, the beveled ledge 136 may include one or more slots or discontinuities. Such slots or discontinuities may have sidewalls that are coextensive with portions of the one or more distal sidewalls 140. In other words, when viewed along the longitudinal axis 128, the beveled ledge 136 may appear to define a circumference or perimeter with one or more breaks or discontinuities. Still further, the beveled ledge 136 may include a plurality of protrusions extending toward the longitudinal axis 128 with spaces or slots in between. In other words, when viewed along the longitudinal axis 128, the beveled ledge 136 may appear to define crenellations along the plurality of sidewalls 138, 140.

The feedthrough pin 146 extends through the ferrule passageway 130 and is coupled to the one or more proximal sidewalls 138. The feedthrough pin 146 may include any suitable conductive material or materials. The feedthrough pin 146 may include, for example, copper, silver, gold, niobium, titanium, aluminum, or other conductive materials. In one or more embodiments, the feedthrough pin 146 includes niobium. The feedthrough pin 146 may provide an electrical connection between electrical circuits or devices within a hermetically sealed enclosure to electrical circuits or devices outside of the hermitically sealed enclosure. In other words, the feedthrough pin 146 may facilitate operative coupling between electrical circuits or devices within the hermetically sealed enclosure and electrical circuits or devices outside of the hermetically sealed enclosure.

The feedthrough pin 146 may be mechanically coupled to the one or more proximal sidewalls 138 by an insulative material 148. The insulative material 148 may form a hermetic seal between the feedthrough pin 146 and the ferrule body 122. The insulative material 148 may include any suitable non-conductive material or materials. The insulative material 148 may include, for example, glass, sapphire, ceramics, or other non-conductive materials capable of forming a hermetic seal between the feedthrough pin 146 and the ferrule body 122. In at least one embodiment, the insulative material 148 is a glass seal. The insulative material 148 may have a high electrical resistance. In at least one embodiment, the insulative material 148 has an electrical resistance of at least 50 giga-ohms.

The capacitor 142 is disposed in the distal passage portion 134 and is electrically coupled to the feedthrough pin 146 and the one or more distal sidewalls 140. The capacitor 142 may be coupled to the feedthrough pin 146 and the one or more distal sidewalls 140 via conductive material 144. The conductive material may include, for example, solder, conductive paste, conductive epoxy, fused conductive particles, etc. The conductive material 144 may include any suitable conductive material or materials. The conductive material may include, for example, copper, gold, tin, lead, silver, indium, or other conductive materials.

The capacitor 142 may include at least one positive terminal and at least one negative terminal. Terminals of the capacitor may be referred to generically (e.g., first terminal, second terminal, etc.) without specifying the polarity of such terminals. The particular polarity and associated connections may depend on the electrical circuits or devices electrically coupled to the feedthrough pin 146. The capacitor 142 may include a first terminal electrically and mechanically coupled to at least a portion of the one or more distal sidewalls 140. In other words, the first terminal of the capacitor 142 may be electrically and mechanically coupled to the ferrule body 122. The capacitor 142 may include a second terminal electrically and mechanically coupled to the feedthrough pin 146. Although the capacitor 142 may provide an electrical coupling between the ferrule body 122 and the feedthrough pin 146, a high DC electrical resistance may still exist between the ferrule body 122 and the feedthrough pin 146. In at least one embodiment, the DC electrical resistance between the feedthrough pin 146 and the ferrule body 122 is at least 50 giga-ohms.

The capacitor 142 may at least partially surround a portion of the feedthrough pin 146. In other words, the feedthrough pin 146 may extend through a gap, opening, or hole in the capacitor 142. In at least one embodiment, the capacitor completely surrounds a portion of the feedthrough pin 146. The capacitor 142 may be seated on or coupled to the beveled ledge 136. The beveled ledge 136 may have a diameter or cross-sectional area that prevents the capacitor 142 from moving into the proximal passage portion 132. Accordingly, the beveled ledge 136 may position the capacitor 142 such that a space or gap is disposed between the capacitor 142 and the insulative material 148. However, the beveled ledge 136 may be shaped such that the capacitor 142 and the beveled ledge cannot have a 360 degree seal between them.

At least a portion of the beveled ledge 136 may define a diameter or cross-sectional area of the ferrule passageway 130 that is smaller than an outer diameter or cross-sectional area of the capacitor 142. For example, a first portion of the beveled surface 137 may define a diameter of the ferrule passageway 130 greater than an outer diameter of the capacitor 142 and a second portion of the beveled surface may define a diameter of the ferrule passageway 130 that is smaller than the outer diameter of the capacitor 142. Additionally, the capacitor 142 may be biased to one side of the distal passage portion 134 as shown in FIG. 4. In fact, the beveled ledge 136 may facilitate the capacitor 142 being biased to one side of the distal passage portion 134 by providing an air gap 143 between the capacitor 142 and the beveled ledge 136.

The feedthrough component 120 may further include an air gap 143 between the capacitor 142 and the beveled ledge 136 that defines a passageway between the distal passage portion 134 and a portion of the proximal passage portion 132. The air gap 143 may allow for fluid communication between the distal passage portion 134 and the portion of the proximal passage portion 132. The air gap 143 may provide a fluid path of least resistance between the distal passage portion 134 and the portion of the proximal passage portion 132. In other words, movement of air or gas between the distal passage portion 134 and the portion of the proximal passage portion 132 may be facilitated through the air gap 143 rather than through liquified conductive material 144. The air gap 143 may be maintained when the conductive material 144 is melted or liquified, thereby preventing such liquified conductive material 144 from being pulled into the space between the capacitor 142 and the insulative material 148. Accordingly, the air gap 143 provided by the beveled ledge 136 may prevent or reduce occurrences of electrical shorts between the feedthrough pin 146 and the ferrule body 122. Thus, the feedthrough component 120 may provide various benefits compared to existing feedthrough ferrules such as, for example, feedthrough component 100 of FIGS. 1 and 2.

Figure 10:
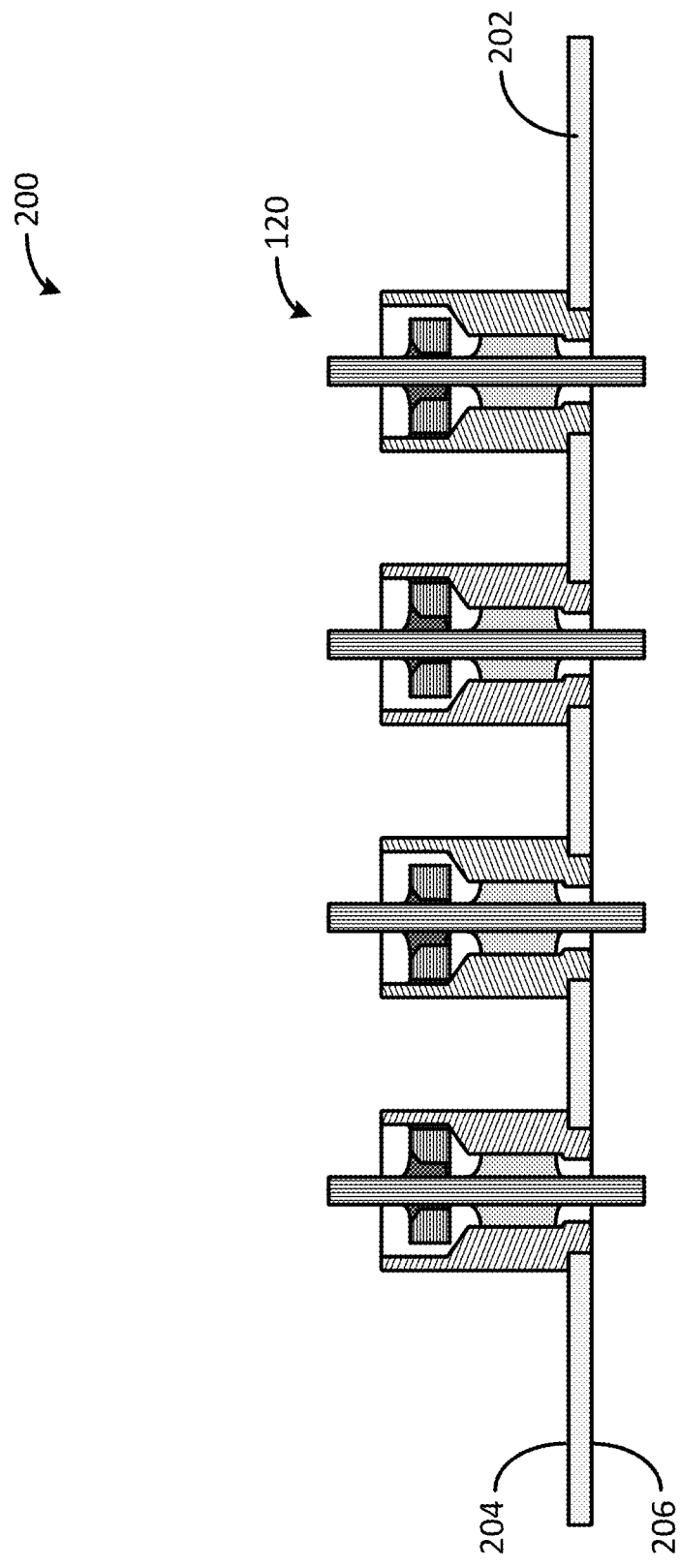
FIG. 10 is a schematic cross-sectional view of a feedthrough assembly that includes feedthrough components that include a beveled ledge.
Figure 11:
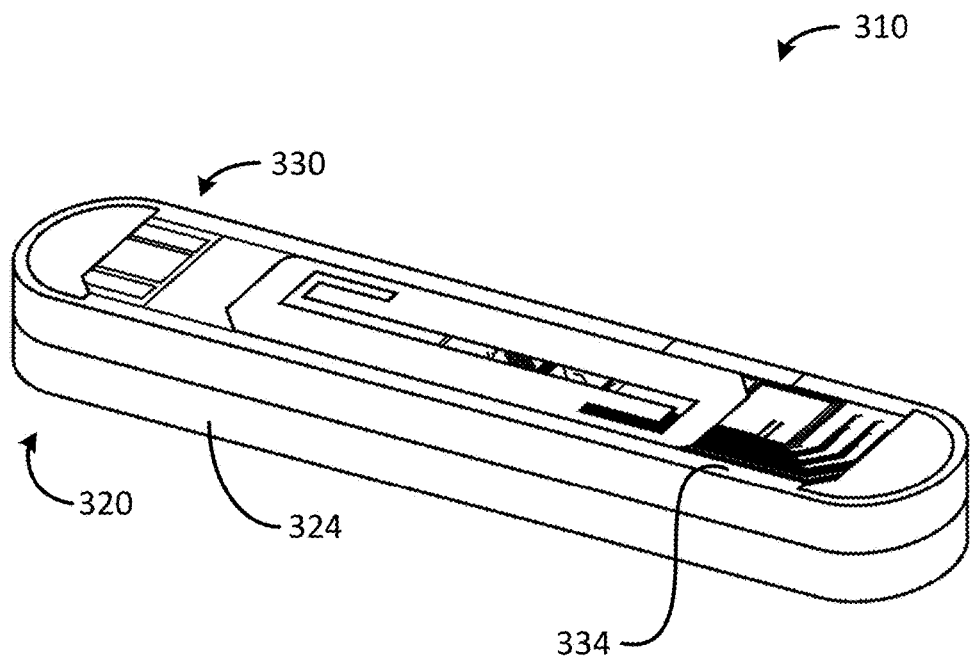
FIG. 11 is a schematic perspective view of an implantable medical device that includes feedthrough components that include a beveled ledge.
Figure 12:
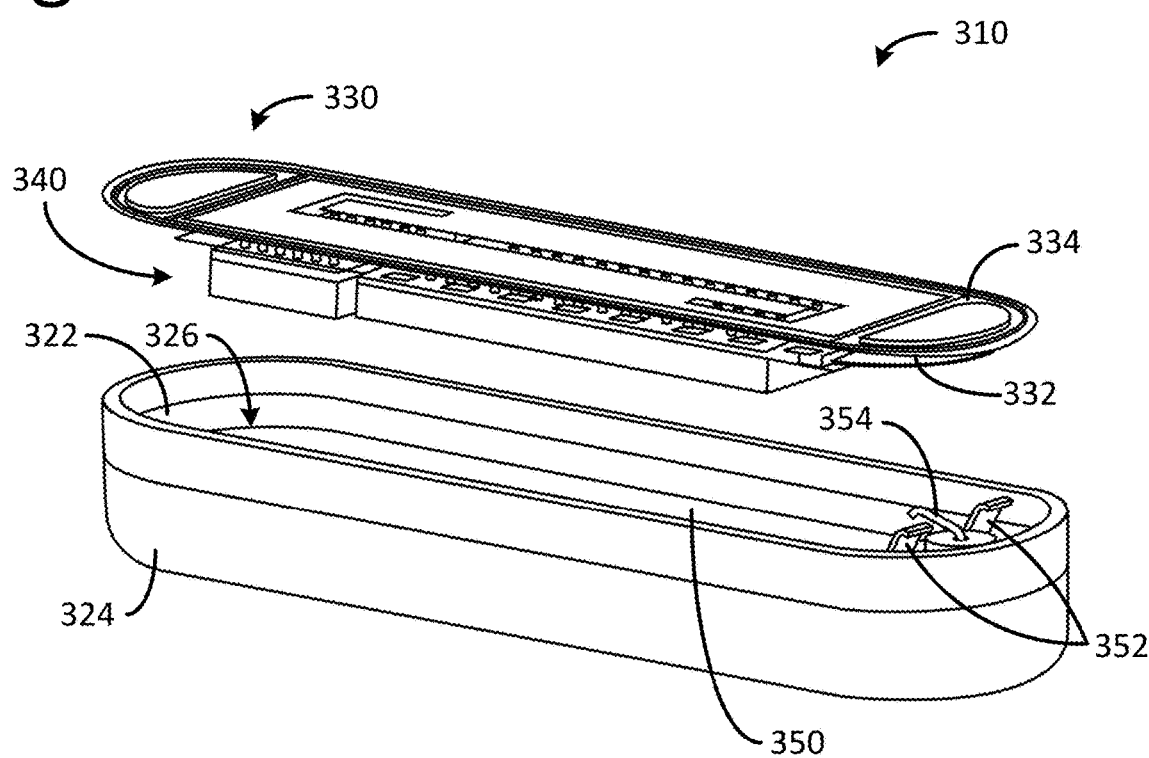
FIG. 12 is a schematic exploded view of an implantable medical device that includes feedthrough components that include a beveled ledge.

The feedthrough component 120 may be used in feedthrough assemblies and/or implantable medical devices as shown in FIGS. 10-12. FIG. 10 shows a feedthrough assembly 200 that includes feedthrough components 120. FIGS. 11 and 12 show an implantable medical device 310 that also includes feedthrough components 120.

The feedthrough assembly 200 includes a substrate 202 and one or more feedthrough components 120 extending through the substrate 202. The substrate 202 has a thickness that extends between a first major surface 204 and a second major surface 206. Each of the one or more feedthrough components 120 may extend through the first major surface 204 and the second major surface 206. The substrate 202 may include any suitable material or materials such as, for example, glass, transparent ceramic, or sapphire. Transparent ceramics may include, for example, alumina ($Al_2O_3$), nanocrystalline yttria-stabilized zirconia (nc-YSZ), or other biostable transparent ceramics. In at least one embodiment, the substrate 202 includes sapphire. The substrate 202 may take on any suitable shape or shapes and have any suitable dimensions. Generally, the substrate 202 may be shaped to fit in a housing of a device (e.g., the implantable medical device 310 of FIGS. 11 and 12) or an opening of such housing. The substrate 202 may be suitable for being welded or brazed to such a housing to form a hermetic seal.

FIGS. 11 and 12 are various schematic views of one embodiment of an implantable medical device 310 that may utilize one or more feedthrough ferrules with a beveled ledge as described herein (e.g., feedthrough component 120 of FIGS. 2-9). FIG. 11 is a schematic perspective view of the implantable medical device 310. FIG. 12 is a schematic exploded view of the implantable medical device 310. The implantable medical device 310 includes a housing 320 and a substrate 330 (e.g., substrate 202 of FIG. 10). The housing 320 includes an inner surface 322 and an outer surface 324. Further, the substrate 330 includes a first major surface 332 and a second major surface 334. The implantable medical device 310 also includes at least one electronic device 340 disposed on the first major surface 332 of the substrate 330. The implantable medical device 310 also includes a power source 350 that is disposed at least partially within the housing 320. In one or more embodiments, the power source 350 can be disposed within a cavity 326 of the housing 320. The power source 350 includes one or more power source contacts 352, 354.

The substrate 330 can be sealed to the housing 320 to form a hermetic seal as described in co-owned U.S. Pat. No. 10,880,009 to Nielsen et al. and entitled METHOD OF FORMING A SEALED PACKAGE, which is incorporated by reference in its entirety. In one or more embodiments, the substrate 330 can be hermetically sealed to the housing 320. Further, in one or more embodiments, the substrate 330 can be sealed to the housing 320 such that a non-bonded electrical connection can be formed between one or more device contacts (not shown) and one or more power source contacts 352, 354. Still further, the substrate 330 may include one or more feedthrough ferrules (e.g., feedthrough component 120 of FIGS. 1-9) with a beveled ledge 136 (e.g., beveled ledge 136 of FIGS. 2-9) as described herein, to provide electrical connections to electronic devices 340 located in the housing 320 and external components such as leads, sensors, etc.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A feedthrough component comprising:
a feedthrough ferrule comprising:
 a ferrule body extending from a proximal end to a distal end along a longitudinal axis of the feedthrough ferrule;
 a ferrule passageway extending through the ferrule body and defined by a plurality of sidewalls, the ferrule passageway comprising:
  a proximal passage portion defined by one or more proximal sidewalls of the plurality of sidewalls and extending along the longitudinal axis;
  a distal passage portion defined by one or more distal sidewalls and extending along the longitudinal axis; and
  a beveled ledge disposed between the proximal passage portion and the distal passage portion and extending from the one or more distal sidewalls toward the longitudinal axis of the feedthrough ferrule, the beveled ledge comprising a beveled surface extending toward the longitudinal axis, wherein a normal to the beveled surface intersects the longitudinal axis;
a feedthrough pin extending through the ferrule passageway and coupled to the one or more proximal sidewalls; and
a capacitor disposed in the distal passage portion and electrically coupled to the feedthrough pin and the one or more distal sidewalls;
wherein a first portion of the beveled surface defines a diameter of the ferrule passageway that is greater than an outer diameter of the capacitor and a second portion of the beveled surface defines a diameter of the ferrule passageway that is smaller than the outer diameter of the capacitor.

2. The feedthrough component of claim 1, wherein the distal passage portion is in fluid communication with at least a portion of the proximal passage portion.

3. The feedthrough component of claim 1, wherein the normal to the beveled surface defines an acute angle relative to the longitudinal axis of at least 10 degrees and no greater than 70 degrees.

4. The feedthrough component of claim 1, wherein the beveled ledge further comprises a first surface extending from the one or more distal sidewalls and the beveled surface extends from the first surface, wherein the first surface and the beveled surface are non-coplanar.

5. The feedthrough component of claim 1, wherein the beveled surface is planar.

6. The feedthrough component of claim 1, wherein the beveled surface is convex.

7. The feedthrough component of claim 1, wherein the beveled ledge defines a tapering frustoconical sidewall.

8. The feedthrough component of claim 1, further comprising an air gap between the capacitor and the beveled ledge defining a passageway between the distal passage portion and a portion of the proximal passage portion.

9. The feedthrough component of claim 1, wherein a cross-sectional area of the distal passage portion arranged perpendicular to the longitudinal axis is greater than a cross-sectional area of the proximal passage portion arranged perpendicular to the longitudinal axis.

10. The feedthrough component of claim 1, wherein the ferrule body is cylindrical.

11. The feedthrough component of claim 1, further comprising an insulative material mechanically coupling the feedthrough pin to the one or more proximal sidewalls and forming a hermetic seal between the feedthrough pin and the ferrule body.

12. The feedthrough component of claim 1, wherein the beveled surface extends from a first endpoint to a second endpoint and wherein a plane that intersects both the first endpoint of the beveled surface and the second endpoint of the beveled surface forms an acute angle with the longitudinal axis of at least 10 degrees and no less than 80 degrees.

13. The feedthrough component of claim 1, wherein the capacitor comprises:
a first terminal electrically and mechanically coupled to at least a portion of the one or more distal sidewalls; and
a second terminal electrically and mechanically coupled to the feedthrough pin.

14. The feedthrough component of claim 1, wherein a direct current (DC) electrical resistance between the feedthrough pin and the ferrule body is at least 50 giga-ohms.

15. The feedthrough component of claim 1, wherein the ferrule body comprises titanium.

16. A feedthrough assembly comprising:
a substrate; and
one or more feedthrough components extending through the substrate, each of the one or more feedthrough components comprising:
   a feedthrough ferrule comprising:
      a ferrule body extending from a proximal end to a distal end along a longitudinal axis of the feedthrough ferrule;
      a ferrule passageway extending through the ferrule body and defined by a plurality of sidewalls, the ferrule passageway comprising:
         a proximal passage portion defined by one or more proximal sidewalls of the plurality of sidewalls and extending along the longitudinal axis;
         a distal passage portion defined by one or more distal sidewalls and extending along the longitudinal axis; and
         a beveled ledge disposed between the proximal passage portion and the distal passage portion and extending from the one or more distal sidewalls toward the longitudinal axis of the feedthrough ferrule, the beveled ledge comprising a beveled surface extending toward the longitudinal axis, wherein a normal to the beveled surface intersects the longitudinal axis;
   a feedthrough pin extending through the ferrule passageway and mechanically coupled to the one or more proximal sidewalls by an insulative material, wherein the insulative material forms a hermetic seal between the feedthrough pin and the ferrule body; and
   a capacitor disposed in the distal passage portion and electrically coupled to the feedthrough pin and the one or more distal sidewalls;
   wherein the beveled ledge is configured to position the capacitor such that a space or gap is disposed between the capacitor and the insulative material.

17. The feedthrough assembly of claim 16, wherein the one or more feedthrough components each form a hermetic seal with the substrate.

18. The feedthrough assembly of claim 16, wherein the substrate comprises titanium.

19. An implantable medical device comprising:
a feedthrough housing;
a substrate hermetically sealed to the feedthrough housing; and
one or more feedthrough components hermetically sealed to the substrate and extending through the substrate, each of the one or more feedthrough components comprising:
   a feedthrough ferrule comprising:
      a ferrule body extending from a proximal end to a distal end along a longitudinal axis of the feedthrough ferrule;
      a ferrule passageway extending through the ferrule body and defined by a plurality of sidewalls, the ferrule passageway comprising:
         a proximal passage portion defined by one or more proximal sidewalls of the plurality of sidewalls and extending along the longitudinal axis;
         a distal passage portion defined by one or more distal sidewalls and extending along the longitudinal axis; and
         a beveled ledge disposed between the proximal passage portion and the distal passage portion and extending from the one or more distal sidewalls toward the longitudinal axis of the feedthrough ferrule, the beveled ledge comprising a beveled surface extending toward the longitudinal axis, wherein a normal to the beveled surface intersects the longitudinal axis;
   a feedthrough pin extending through the ferrule passageway and coupled to the one or more proximal sidewalls; and
   a capacitor disposed in the distal passage portion and electrically coupled to the feedthrough pin and the one or more distal sidewalls, wherein the capacitor is seated on the beveled ledge.

20. The implantable medical device of claim 19, wherein at least one feedthrough component comprises an air gap between the capacitor and the beveled ledge that defines a passageway between the distal passage portion and a portion of the proximal passage portion, wherein the air gap is configured to allow for fluid communication between the distal passage portion and the portion of the proximal passage portion.

* * * * *